(12) United States Patent
Grindstaff et al.

(10) Patent No.: US 9,097,633 B2
(45) Date of Patent: Aug. 4, 2015

(54) REACTOR CELL ASSEMBLY FOR USE IN SPECTROSCOPY AND MICROSCOPY APPLICATIONS

(71) Applicants: Quirinus Grindstaff, Oak Ridge, TN (US); Ashley Clinton Stowe, Knoxville, TN (US); Norm Smyrl, Knoxville, TN (US); Louis Powell, Oak Ridge, TN (US); Sam McLane, Oak Ridge, TN (US)

(72) Inventors: Quirinus Grindstaff, Oak Ridge, TN (US); Ashley Clinton Stowe, Knoxville, TN (US); Norm Smyrl, Knoxville, TN (US); Louis Powell, Oak Ridge, TN (US); Sam McLane, Oak Ridge, TN (US)

(73) Assignee: Consolidated Nuclear Security, LLC, Reston, VA (US)

( * ) Notice: Subject to any disclaimer, the term of this patent is extended or adjusted under 35 U.S.C. 154(b) by 0 days.

(21) Appl. No.: 13/834,811

(22) Filed: Mar. 15, 2013

(65) Prior Publication Data
US 2014/0273266 A1 Sep. 18, 2014

(51) Int. Cl.
*G01N 21/00* (2006.01)
*G01N 1/44* (2006.01)
*G01N 21/03* (2006.01)
*B01L 7/00* (2006.01)
*G02B 21/00* (2006.01)

(52) U.S. Cl.
CPC ............... *G01N 1/44* (2013.01); *G01N 21/03* (2013.01); *B01L 7/00* (2013.01); *G01N 21/0332* (2013.01); *G01N 2021/0325* (2013.01); *G01N 2021/0389* (2013.01); *G02B 21/00* (2013.01); *Y10T 436/25* (2015.01)

(58) Field of Classification Search
CPC ......... G01N 21/00; G01N 1/44; G01N 21/03; G01N 21/332; G01N 2021/325; G01N 2021/0389; G02B 1/00; Y10T 436/25; B01L 7/00
USPC ......................................................... 436/174
See application file for complete search history.

(56) References Cited

U.S. PATENT DOCUMENTS

| | | | |
|---|---|---|---|
| 4,707,086 A * | 11/1987 | Dahan et al. ................... | 359/398 |
| 7,255,474 B2 | 8/2007 | Cong et al. | |
| 8,309,929 B2 | 11/2012 | Bond et al. | |
| 2006/0231204 A1* | 10/2006 | Elliott et al. ................ | 156/345.5 |
| 2008/0233017 A1* | 9/2008 | Sato et al. ....................... | 422/129 |
| 2009/0241232 A1* | 9/2009 | Mack et al. ..................... | 850/26 |
| 2009/0303308 A1* | 12/2009 | Itoh et al. ....................... | 347/256 |

* cited by examiner

*Primary Examiner* — Christopher A Hixson
*Assistant Examiner* — Emily Berkeley
(74) *Attorney, Agent, or Firm* — Clements Bernard PLLC; Christopher L. Bernard; Lawrence A. Baratta, Jr.

(57) ABSTRACT

The present disclosure provides a reactor cell assembly that utilizes a novel design and that is wholly or partially manufactured from Aluminum, such that reactions involving Hydrogen, for example, including solid-gas reactions and thermal decomposition reactions, are not affected by any degree of Hydrogen outgassing. This reactor cell assembly can be utilized in a wide range of optical and laser spectroscopy applications, as well as optical microscopy applications, including high-temperature and high-pressure applications. The result is that the elucidation of the role of Hydrogen in the reactions studied can be achieved. Various window assemblies can be utilized, such that high temperatures and high pressures can be accommodated and the signals obtained can be optimized.

23 Claims, 3 Drawing Sheets

Heating Post 24
(Whole or Partial)

Thermal Break — 40

Other Components
of Reactor Cell
Assembly 10

*FIG. 3*

REACTOR CELL ASSEMBLY FOR USE IN SPECTROSCOPY AND MICROSCOPY APPLICATIONS

STATEMENT REGARDING FEDERALLY SPONSORED RESEARCH OR DEVELOPMENT

The U.S. Government has rights to the present disclosure pursuant to Contract No. AC05-00OR22800 between the U.S. Department of Energy and Babcock and Wilcox Technical Services Y-12, LLC.

FIELD OF THE DISCLOSURE

The present disclosure relates generally to the spectroscopy and microscopy fields. More specifically, the present disclosure relates to a reactor cell assembly for use in spectroscopy and microscopy applications, especially high-temperature applications where it is desirable to limit Hydrogen outgassing from the reactor cell assembly.

BACKGROUND OF THE DISCLOSURE

Reactions involving Hydrogen, including solid-gas reactions and thermal decomposition reactions, are especially challenging in spectroscopy and microscopy applications, as small amounts of Hydrogen outgassing from a stainless steel reactor cell assembly, for example, can affect the reactions and skew results. Such reactions are typically studied in a reactor cell assembly that includes a sample holder of some sort disposed within a well including a window of some sort. The body of the reactor cell assembly includes ports and conduits suitable for creating a vacuum within the well, as well as providing both a purge (i.e. inert) gas and a reactive gas to the sample.

What is still needed in the art is an improved reactor cell assembly that, while being functional in all other respects, does not exhibit any degree of Hydrogen outgassing, such that reactions involving Hydrogen, for example, including solid-gas reactions and thermal decomposition reactions, are not affected thereby.

BRIEF SUMMARY OF THE DISCLOSURE

In various exemplary embodiments, the present disclosure provides a reactor cell assembly that utilizes a novel design and that is wholly or partially manufactured from Aluminum, such that reactions involving Hydrogen, for example, including solid-gas reactions and thermal decomposition reactions, are not affected by any degree of Hydrogen outgassing. This reactor cell assembly can be utilized in a wide range of optical and laser spectroscopy applications, as well as optical microscopy applications, including high-temperature and high-pressure applications. The result is that the elucidation of the role of Hydrogen in the reactions studied can be achieved. Various window assemblies can be utilized, such that high temperatures and high pressures can be accommodated and the signals obtained can be optimized.

In one exemplary embodiment, the present disclosure provides a reactor cell assembly for use in spectroscopy and microscopy applications, including: a body structure; a sample retention structure (i.e. a collar structure, annular structure, or internal wall structure) either coupled to or integrally formed with the body structure, wherein the sample retention structure is configured to contain a sample to be reacted that is selectively disposed therein (within a well defined thereby); a sample holder (i.e. a heating post including or coupled to a structure for holding/retaining the sample to be reacted) either coupled to or integrally formed with the body structure and disposed within the sample retention structure, wherein the sample holder is thermally coupled to a heating device and configured to deliver heat to the sample to be reacted; and a window assembly coupled to the sample retention structure; wherein the window assembly is sufficiently transparent to radiation such that spectroscopy and/or microscopy can be performed. The body structure defines a plurality of fluid transfer paths fluidly coupling an exterior of the body structure to an interior of the sample retention structure. Preferably, the body structure, the sample retention structure, and at least a portion of the sample holder are manufactured at least in part from Aluminum. The sample holder includes a heating device disposed therein. Optionally, the sample holder includes a portion that is manufactured from an insulating material, such that at least a portion of the sample holder is thermally isolated from at least a portion of the body structure. Alternatively, the reactor cell assembly also includes an insulating material disposed between at least a portion of the sample holder and at least a portion of the body structure. The window assembly is at least partially manufactured from glass, quartz, ZnSe, or sapphire, depending upon the application of interest. The reactor cell assembly further includes one or more posts coupled to the plurality of fluid transfer paths within the interior of the sample retention structure.

In another exemplary embodiment, the present disclosure provides a method for providing a reactor cell assembly for use in spectroscopy and microscopy applications, including: providing a body structure; providing a sample retention structure (i.e. a collar structure, annular structure, or internal wall structure) either coupled to or integrally formed with the body structure, wherein the sample retention structure is configured to contain a sample to be reacted that is selectively disposed therein (within a well defined thereby); providing a sample holder (i.e. a heating post including or coupled to a structure for holding/retaining the sample to be reacted) either coupled to or integrally formed with the body structure and disposed within the sample retention structure, wherein the sample holder is thermally coupled to a heating device and configured to deliver heat to the sample to be reacted; and providing a window assembly coupled to the sample retention structure; wherein the window assembly is sufficiently transparent to radiation such that spectroscopy and/or microscopy can be performed. The body structure defines a plurality of fluid transfer paths fluidly coupling an exterior of the body structure to an interior of the sample retention structure. Preferably, the body structure, the sample retention structure, and at least a portion of the sample holder are manufactured at least in part from Aluminum. The sample holder includes a heating device disposed therein. Optionally, the sample holder includes a portion that is manufactured from an insulating material, such that at least a portion of the sample holder is thermally isolated from at least a portion of the body structure. Alternatively, the method also includes providing an insulating material disposed between at least a portion of the sample holder and at least a portion of the body structure. The window assembly is at least partially manufactured from glass, quartz, ZnSe, or sapphire, depending upon the application of interest. The method further includes providing one or more posts coupled to the plurality of fluid transfer paths within the interior of the sample retention structure.

BRIEF DESCRIPTION OF THE DRAWINGS

The present disclosure is illustrated and described herein with reference to the various drawings, in which like refer

FIG. 3 is a schematic diagram illustrating one exemplary embodiment of a compound sample support post that can be utilized with the reactor cell assembly of the present disclosure.

DETAILED DESCRIPTION OF THE DISCLOSURE

Figure 1:
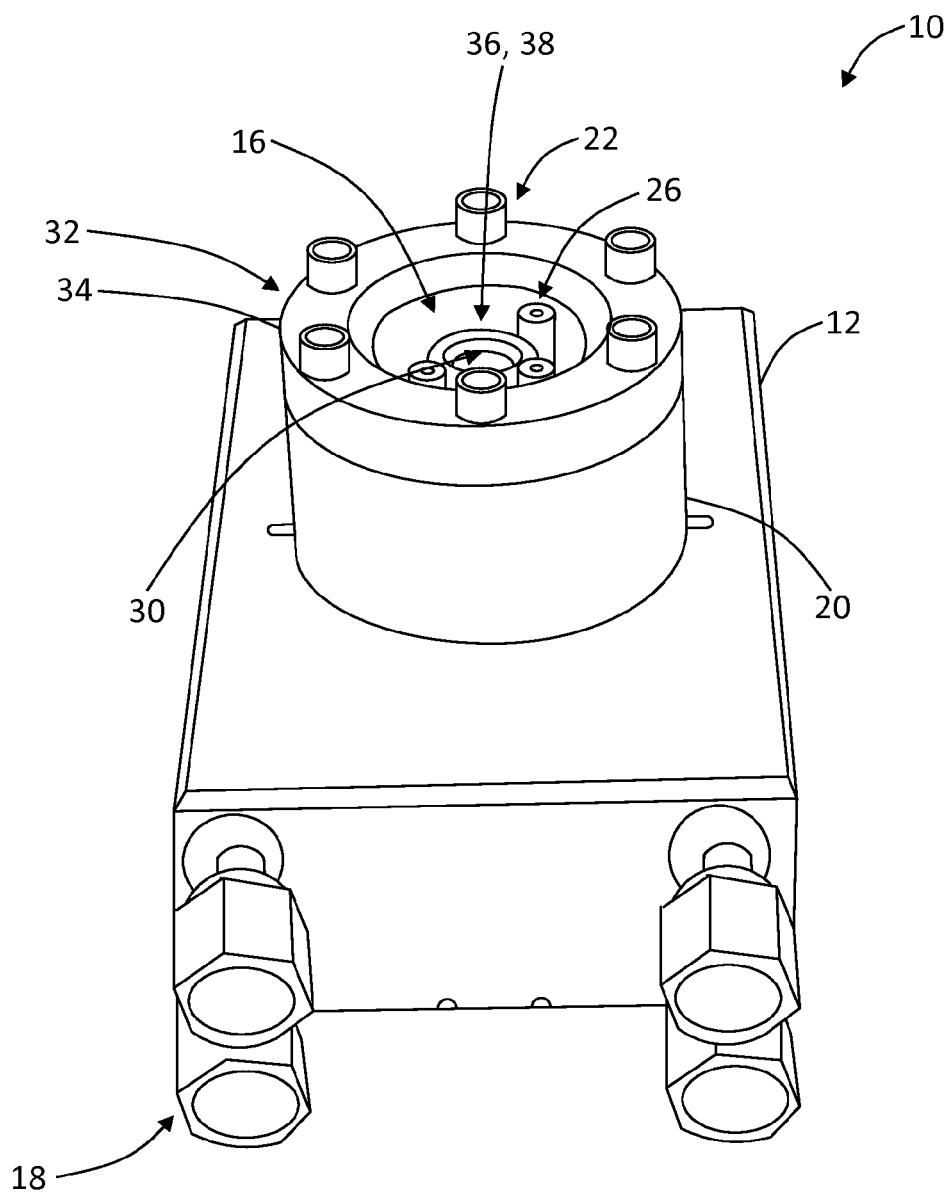
- FIG. 1 is a perspective view of one exemplary embodiment of the reactor cell assembly of the present disclosure in an assembled state.
Figure 2:
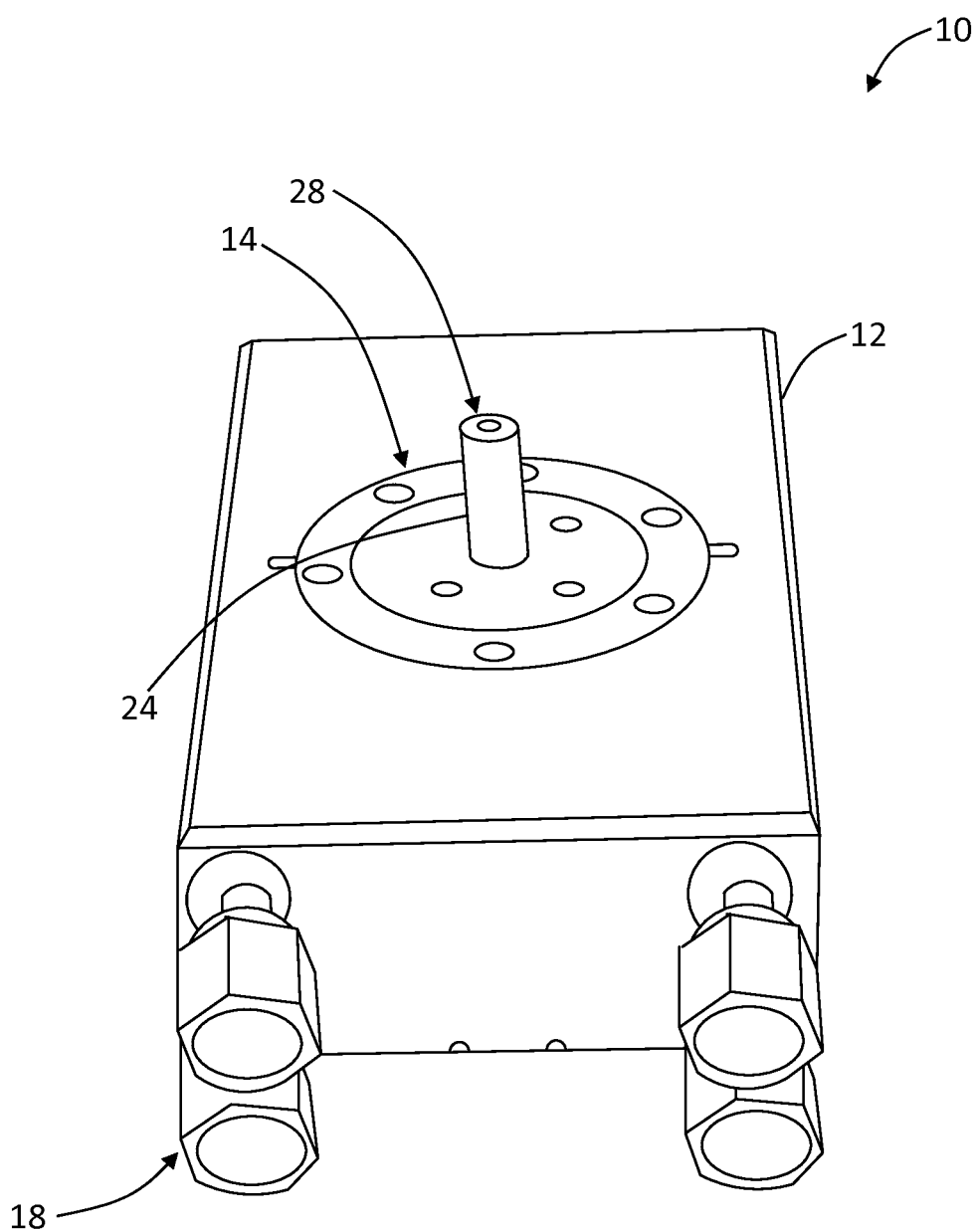
FIG. 2 is a perspective view of one exemplary embodiment of the reactor cell assembly of the present disclosure in a partially unassembled state.

Referring specifically to FIGS. 1 and 2, in one exemplary embodiment, the present disclosure provides a reactor cell assembly 10 that includes a base structure 12 having a surface 14 (FIG. 2) defining at least a portion of a well 16 (FIG. 1) and a plurality of ports 18 and conduits (not illustrated) coupled thereto and defined thereby. In this exemplary embodiment, the well 16 is also at least partially defined by a collar structure 20 (FIG. 1) that is secured to the base structure 12 using a plurality of bolts 22 (FIG. 1). It will be appreciated by those of ordinary skill in the art that the well 16 could be entirely formed by the base structure 12, the collar structure 20, and/or another suitable structure. In use, a sample to be reacted (not illustrated) is disposed within the well 16 and variously exposed to a vacuum or pressurized condition, a purge (i.e. inert) gas, and/or a reactive gas that are provided through the plurality of ports 18 and conduits. Thus, the plurality of ports 18 and conduits provide fluid (i.e. gas) communication paths from the exterior of the base structure 12, through the base structure 12, and to the sample space defined by the well 16. A gas analysis instrument may also be fluidly coupled to the sample space defined by the well 16 via one of the plurality of ports 18 and conduits. Accordingly, the reactor cell assembly 10 is selectively coupled to the appropriate vacuum/pressure control systems, purge gas sources and control systems, reactive gas sources and control systems, etc., as well as temperature control systems and the aforementioned gas analysis instruments.

Within the well 16, a heating post 24 (FIG. 2) having a hollow interior and at least one open end and a plurality of fluid communication posts 26 (FIG. 1) each having a hollow interior and two open ends are fluidly coupled to the plurality of ports 18 and conduits, such as by being screwed into appropriate holes manufactured into the base structure 12. The sample to be reacted is disposed either on an appropriate sample receiving area 28 (FIG. 2) manufactured into a closed end of the heating post 24 or on a sample receiving structure 30 (FIG. 1) that is coupled to an end of the heating post 24 distal to the base structure 12. Collectively, the heating post 24 and the plurality of fluid communication posts 26 hold the sample to be reacted at an elevated position within the well 16, and extend the conduits to an area near this elevated position. A split-sheath heater (not illustrated) or the like is disposed within the interior of the heating post 24, preferably with its heating zone proximate the sample to be reacted, such that the sample to be reacted can be selectively heated through the heating post 24.

In this exemplary embodiment, the top of the well 16 is closed using a window assembly 32 (FIG. 1), optionally including a frame 34 (FIG. 1) defining a port 36 (FIG. 1) and a window 38 (FIG. 1). The window assembly 32 is secured to the collar structure 20 using the plurality of bolts 22, for example. One or more gaskets (not illustrated) can be disposed between the body structure 12, the collar structure 20, and/or the window assembly 32, such that a sealed environment is created within the well 16. It will be appreciated by those of ordinary skill in the art that the components of the reactor cell assembly 10 of the present disclosure, as described to this point are all in thermal communication and can be separate components or integrally formed. Although not central to the present disclosure, the base structure 12 may further include other voids, conduits, etc. for the purpose of, for example, placing, accessing, and/or operating the heater (i.e. a thermowell and paths for connections to a heater controller or the like).

The reactor cell assembly 10 illustrated and described has a generally rectangular base structure 12, a generally annular collar structure 20 and window assembly 32, a generally tubular heating post 24, and generally tubular fluid communication posts 26; however, it will be appreciated by those of ordinary skill in the art that other suitable shapes and configurations could be utilized. In general, the reactor cell assembly 10 has dimensions on the order of centimeters or inches, although it could be smaller or larger as required for a specific application.

The base structure 12 can be machined from a single billet of Aluminum to provide embedded gas paths. The other components of the reactor cell assembly 10 can also be machined from Aluminum. Alternatively, in applications that so allow, some or all of the components can be machined from stainless steel, monel, or another metal, or the like. Stainless steel is the most durable and could be used for standard reaction or spectroscopy/microscopy applications. In applications involving acid gasses, such as hydrofluoric acid, monel could be used. For many applications, where Hydrogen is involved, fabrication of the cell from Aluminum, at least in part, is most desirable. Aluminum is a unique fabrication material for spectroscopy/microscopy cells. Stainless steel outgasses Hydrogen, which can either react with a sample or can adversely affect the analysis of the sample within the cell. Thus, Aluminum construction (which does not outgas Hydrogen) provides greater accuracy and better sensitivity than stainless steel construction.

The window assembly 32, and specifically the window 38, can be glass, quartz, ZnSe, or sapphire, depending on the specific application. For example, a quartz window is best suited to Raman spectroscopy applications, a ZnSe window is best suited to infrared spectroscopy applications, and a sapphire window is best suited to high-pressure applications.

Aluminum construction can add unique heat management concerns, which the present disclosure addresses. Heating the sample to be reacted through the heating post 24 coupled to the base structure 12 of the reactor cell assembly 10 also heats the base structure 12 itself. Thus, the entire base structure 12 rather quickly heats to the sample temperature due to the large thermal conductivity of Aluminum. The same is true for other components of the reactor cell assembly 10.

Referring specifically to FIG. 3, in another exemplary embodiment, this heat management concern when using Aluminum is addressed by disposing a thermal break 40, such as a ceramic thermal break or the like, between at least the primary sample-heating portion of the heating post 24 and the base structure 12 and other components of the reactor cell assembly 10, if not about the entire heating post 24. This thermal break 40 can make up a portion of the heating post 24, be an independent structure, be a coating disposed on the heating post 24, etc. Thus, the potentially problematic thermal path has been blocked.

The reactor cell assembly 10 of the present disclosure can be used with any type of sample (powder, liquid, or compressed solid) that is reactive with the environment. Reactions between a sample and reactive gases can be studied over a wide range of temperatures. Further, thermal decomposition can be studied at atmospheric pressure or under high vacuum. High-pressure experiments can also be conducted.

Although the present disclosure has been illustrated and described herein with reference to preferred embodiments and specific examples thereof, it will be appreciated by those of ordinary skill in the art that other embodiments and examples may perform similar functions and/or achieve like results. All such equivalent embodiments and examples are within the spirit and scope of the present disclosure, are contemplated thereby, and are intended to be covered by the following claims, which should be given the benefit of all reasonable equivalents.

What is claimed is:

1. A reactor cell assembly for use in spectroscopy and microscopy applications, comprising:
   a body structure;
   a sample retention structure coupled to the body structure, wherein the sample retention structure is configured to contain a sample to be reacted that is selectively disposed therein;
   a sample holder coupled to the body structure and disposed within the sample retention structure, wherein the sample holder is thermally coupled to a heating device and configured to deliver heat to the sample to be reacted, and wherein the sample holder comprises a post structure protruding from a surface of one of the body structure and the sample retention structure;
   a plurality of fluid communication posts disposed concentrically about the post structure of the sample holder and protruding from the surface from which the post structure of the sample holder protrudes parallel to the post structure of the sample holder; and
   a window assembly coupled to the sample retention structure;
   wherein the window assembly is sufficiently transparent to radiation such that spectroscopy or microscopy can be performed.

2. The reactor cell assembly of claim 1, wherein the body structure defines one or more fluid transfer paths fluidly coupling an exterior of the body structure to an interior of the sample retention structure through the one or more fluid communication posts.

3. The reactor cell assembly of claim 1, wherein the body structure, the sample retention structure, and at least a portion of the sample holder are manufactured from Aluminum.

4. The reactor cell assembly of claim 1, wherein the sample holder comprises a heating device disposed therein.

5. The reactor cell assembly of claim 1, wherein the sample holder comprises a portion that is manufactured from an insulating material, such that at least a portion of the sample holder is thermally isolated from at least a portion of the body structure.

6. The reactor cell assembly of claim 1, further comprising an insulating material disposed between at least a portion of the sample holder and at least a portion of the body structure.

7. The reactor cell assembly of claim 1, wherein the window assembly is at least partially manufactured from a material selected from the group consisting of glass, quartz, ZnSe, and sapphire.

8. A method for providing a reactor cell assembly for use in spectroscopy and microscopy applications, comprising:
   providing a body structure;
   providing a sample retention structure coupled to the body structure, wherein the sample retention structure is configured to contain a sample to be reacted that is selectively disposed therein;
   providing a sample holder coupled to the body structure and disposed within the sample retention structure, wherein the sample holder is thermally coupled to a heating device and configured to deliver heat to the sample to be reacted, and wherein the sample holder comprises a post structure protruding from a surface of one of the body structure and the sample retention structure;
   disposing a sample on the sample holder;
   providing a plurality of fluid communication posts disposed concentrically about the post structure of the sample holder and protruding from the surface from which the post structure of the sample holder protrudes parallel to the post structure of the sample holder;
   providing a fluid to the sample through the one or more fluid communication posts;
   providing a window assembly coupled to the sample retention structure, wherein the window assembly is sufficiently transparent to radiation such that spectroscopy or microscopy can be performed; and
   performing spectroscopy or microscopy through the window assembly.

9. The method of claim 8, wherein the body structure defines one or more fluid transfer paths fluidly coupling an exterior of the body structure to an interior of the sample retention structure through the one or more fluid communication posts.

10. The method of claim 8, wherein the body structure, the sample retention structure, and at least a portion of the sample holder are manufactured at least in part from Aluminum.

11. The method of claim 8, wherein the sample holder comprises a heating device disposed therein.

12. The method of claim 8, wherein the sample holder comprises a portion that is manufactured from an insulating material, such that at least a portion of the sample holder is thermally isolated from at least a portion of the body structure.

13. The method of claim 8, further comprising providing an insulating material disposed between at least a portion of the sample holder and at least a portion of the body structure.

14. The method of claim 8, wherein the window assembly is at least partially manufactured from a material selected from the group consisting of glass, quartz, ZnSe, and sapphire.

15. A reactor cell assembly for use in spectroscopy and microscopy applications, comprising:
   a body structure;
   a collar structure coupled to the body structure, wherein the collar structure is configured to contain a sample to be reacted that is selectively disposed therein;
   a heating post coupled to the body structure and disposed within the collar structure, wherein the heating post is thermally coupled to a heating device and configured to deliver heat to the sample to be reacted, and wherein the heating post protrudes from a surface of one of the body structure and the collar structure;
   a plurality of fluid communication posts disposed concentrically about the heating post and protruding from the surface from which the heating post protrudes parallel to the heating post; and
   a window assembly coupled to the collar structure;

wherein the window assembly is sufficiently transparent to radiation such that spectroscopy or microscopy can be performed.

16. The reactor cell assembly of claim 15, wherein the body structure, the collar structure, and at least a portion of the heating post are manufactured at least in part from Aluminum.

17. The reactor cell assembly of claim 15, wherein the heating post comprises a heating device disposed therein.

18. The reactor cell assembly of claim 15, further comprising a sample holder coupled to the heating post and configured to hold the sample to be reacted.

19. A reactor cell assembly for use in spectroscopy and microscopy applications, comprising:
   a body structure;
   a sample retention structure coupled to the body structure, wherein the sample retention structure is configured to contain a sample to be reacted that is selectively disposed therein;
   a sample holder coupled to the body structure and disposed within the sample retention structure, wherein the sample holder is thermally coupled to a heating device and configured to deliver heat to the sample to be reacted;
   a plurality of fluid communication posts disposed concentrically about the sample holder and protruding from a surface of the body structure from which the sample holder protrudes parallel to the sample holder; and
   a window assembly coupled to the sample retention structure;
   wherein the window assembly is sufficiently transparent to radiation such that spectroscopy or microscopy can be performed; and
   wherein a portion of the body structure, the sample retention structure, and the sample holder exposed to the sample to be reacted are manufactured from Aluminum such that Hydrogen outgassing is prevented.

20. The reactor cell assembly of claim 19, wherein the sample holder comprises a heating device disposed therein.

21. The reactor cell assembly of claim 19, wherein the sample holder comprises a portion that is manufactured from an insulating material, such that at least a portion of the sample holder is thermally isolated from at least a portion of the body structure.

22. The reactor cell assembly of claim 19, further comprising an insulating material disposed between at least a portion of the sample holder and at least a portion of the body structure.

23. The reactor cell assembly of claim 19, wherein the window assembly is at least partially manufactured from a material selected from the group consisting of glass, quartz, ZnSe, and sapphire.

* * * * *